(12) United States Patent
Yao et al.

(10) Patent No.: US 7,678,950 B2
(45) Date of Patent: Mar. 16, 2010

(54) PROCESS FOR CONVERTING CARBOHYDRATES TO HYDROCARBONS

(75) Inventors: Jianhua Yao, Bartlesville, OK (US); Edward L. Sughrue, II, Bartlesville, OK (US); James B. Kimble, Bartlesville, OK (US); Joseph B. Cross, Bartlesville, OK (US); Marvin M. Johnson, Bartlesville, OK (US); Dhananjay B. Ghonasgi, Bartlesville, OK (US)

(73) Assignee: ConocoPhillips Company, Houston, TX (US)

( * ) Notice: Subject to any disclaimer, the term of this patent is extended or adjusted under 35 U.S.C. 154(b) by 1124 days.

(21) Appl. No.: 11/303,636

(22) Filed: Dec. 16, 2005

(65) Prior Publication Data

US 2007/0142633 A1    Jun. 21, 2007

(51) Int. Cl.
*C07C 1/00* (2006.01)

(52) U.S. Cl. .............. 585/240; 585/408; 585/640; 585/733

(58) Field of Classification Search ......... 585/240, 585/408, 640, 733; 568/863; 127/69, 46.2; 210/674
See application file for complete search history.

(56) References Cited

U.S. PATENT DOCUMENTS

| | | | |
|---|---|---|---|
| 1,411,203 A | 3/1922 | Bright | |
| 1,411,204 A | 3/1922 | Bright | |
| 2,518,235 A | 8/1950 | Hartstra et al. | |
| 3,630,775 A | 12/1971 | Winkler et al. | |
| 3,695,933 A | 10/1972 | Deaton | |
| 3,963,789 A | 6/1976 | Kruse et al. | |
| 3,998,898 A | 12/1976 | Chang et al. | |
| 4,011,278 A | 3/1977 | Plank et al. | |
| 4,148,835 A | 4/1979 | Chen et al. | |
| 4,300,009 A | 11/1981 | Haag et al. | |
| 4,306,106 A | 12/1981 | Kerr et al. | |
| 4,308,411 A | 12/1981 | Frankiewicz | |
| 4,330,625 A * | 5/1982 | Miller et al. | 435/161 |
| 4,380,680 A | 4/1983 | Arena | |
| 4,430,253 A | 2/1984 | Dubeck et al. | |
| 4,503,278 A | 3/1985 | Chen et al. | |
| 4,511,667 A | 4/1985 | Mao et al. | |
| 4,523,928 A | 6/1985 | Hillman et al. | |
| 4,549,031 A * | 10/1985 | Chen et al. | 585/408 |
| 4,933,283 A * | 6/1990 | Chen et al. | 435/166 |
| 4,950,812 A | 8/1990 | Jacobs et al. | |
| 5,194,094 A * | 3/1993 | Ammeraal et al. | 127/69 |
| 5,348,871 A * | 9/1994 | Scott et al. | 435/165 |
| 5,396,016 A | 3/1995 | Jablonski et al. | |
| 5,494,602 A | 2/1996 | Thomaides et al. | |
| 5,600,028 A | 2/1997 | Gubitosa et al. | |
| 5,932,106 A * | 8/1999 | San Miguel Bento | 210/674 |
| 6,121,503 A | 9/2000 | Janssen et al. | |
| 6,570,043 B2 * | 5/2003 | Elliott et al. | 568/863 |
| 2003/0130545 A1 | 7/2003 | Werpy et al. | |
| 2005/0112739 A1 | 5/2005 | Golubkov | |

OTHER PUBLICATIONS

Dao et al., Reactions of Model Compounds of Biomass-Pyrolysis Oils over ZSM-5 Zeolite Catalysts, ACS Symposium Series 376, 1988, pp. 327-341, American Chemical Society.

* cited by examiner

*Primary Examiner*—N. Bhat

(57) ABSTRACT

Processes for the conversion of carbohydrates to gasoline boiling range hydrocarbons, and processes for increasing the solubility of carbohydrates used in such processes are disclosed. The solubility of carbohydrates may be increased by contacting the carbohydrate with an ion-exchange resin. The dissolved product may be hydrogenated and reacted in the present of a catalyst to form a reaction product containing non-aromatic and aromatic gasoline boiling range hydrocarbons.

67 Claims, No Drawings

PROCESS FOR CONVERTING CARBOHYDRATES TO HYDROCARBONS

FIELD OF THE INVENTION

The present invention relates generally to the conversion of carbohydrates to fuel range hydrocarbons.

BACKGROUND OF THE INVENTION

There is a national interest in the discovery of alternative sources of fuels and chemicals, other than from petroleum resources. As the public discussion concerning the availability of petroleum resources and the need for alternative sources continues, it is anticipated that future government mandates will require transportation fuels to include, at least in part, hydrocarbons derived from sources besides petroleum. As such, there is a need to develop alternative sources for hydrocarbons useful for producing fuels and chemicals.

One possible alternative source of hydrocarbons for producing fuels and chemicals is the natural carbon found in plants and animals, such as for example, in the form of carbohydrates. These so-called "natural" carbon resources (or renewable hydrocarbons) are widely available, and remain a target alternative source for the production of hydrocarbons. For example, it is known that carbohydrates and other sugar-based feedstocks can be used to produce ethanol, which has been used in gasohol and other energy applications. However, the use of ethanol in transportation fuels has not proven to be cost effective.

Carbohydrates, however, also can be used to produce fuel range hydrocarbons. The upgrading of biologically derived materials to materials useful in producing fuels is known in the art. However, many carbohydrates (e.g., starch) are undesirable as feed stocks due to the costs associated with converting them to a usable form. In addition, many carbohydrates are known to be "difficult" to convert due to their chemical structure, or that the hydrocarbon product produced is undesirable or will result in low quantities of desirable product. Among the compounds that are stated to be difficult to convert include compounds with low effective hydrogen to carbon ratios, including carbohydrates such as starches and sugars, carboxylic acids and anhydrides, lower glycols, glycerin and other polyols and short chain aldehydes. As such, efforts have been made to convert traditionally difficult to convert materials to hydrocarbons by focusing on methods for increasing the effective hydrogen to carbon ratio of the reactants, including converting oxygenates in the presence of hydrogen, CO, steam, nitrogen, or other reactants, and by employing various catalysts. However, these processes are often complex and are costly, and the reaction products produced as a result of these processes are oftentimes undesirable, or result in low weight percentages, and often result in an increase in undesirable byproducts such as the production of carbon monoxide and carbon dioxide.

In addition, many carbohydrates (such as complex polysaccharides, including corn starch) in their raw form are undesirable as feeds. For example, starch, in its native form, is a solid and as such, prior to use, it is desirable to convert the solid form into a liquid form for ease of processing. However, when starch is combined with liquid, it becomes extremely viscous, making dissolution difficult. As a result, many processes employed only result in the partial hydrolyzation of the carbohydrate starting material, which necessitates addressing the undissolved solid fraction in the reaction zone. In addition, because of the viscosity, it is often required to mix the carbohydrate with large volumes of water and/or chemicals, along with harsh reaction conditions in order to achieve the desired dissolution.

As such, development of a process for increasing the solubility of carbohydrates in the conversion of carbohydrates to hydrocarbons would be a significant contribution to the art. In addition, development of a process for converting carbohydrates to hydrocarbons which yields significant quantities of desirable hydrocarbon products such as aromatics and olefins would be a significant contribution to the art. Furthermore, development of a carbohydrate conversion process resulting in a product with reduced byproducts such as carbon monoxide and carbon dioxide, and coke production, would be a significant contribution to the art.

SUMMARY OF THE INVENTION

Accordingly, it is an object of the present invention to provide a process for increasing the solubility of a carbohydrate, such as for example starch, utilizing ion-exchange resins, for use in a process for the conversion of the carbohydrate to gasoline boiling range hydrocarbons, such as for example non-aromatic and aromatic boiling range hydrocarbons.

A further object of the present invention is to provide an improved process for the conversion of carbohydrates to hydrocarbons, particularly non-aromatic and aromatic gasoline boiling range hydrocarbons, using an improved integrated process which produces an improved yield of reaction products including aromatic gasoline boiling range hydrocarbons, such as for example $C_6$-$C_8$ aromatic hydrocarbons (benzene, toluene, xylene, and ethyl benzene).

A further object of the present invention is to provide a process for converting carbohydrate-containing compounds, including starch, corn syrup, and lactic acid, to non-aromatic and aromatic gasoline boiling range hydrocarbons.

A further object of the present invention is to provide a process for the conversion of carbohydrates to hydrocarbons in which the rate of coke formation and the production of $CO_x$ by-products during such conversion is minimized.

In one embodiment of the present invention, a process is provided for increasing the solubility of a carbohydrate-containing compound, such as a polysaccharide, for example, corn starch, by contacting the carbohydrate-containing compound with an ion-exchange resin in a liquid medium to form a mixture. The mixture is then heated at a temperature sufficient to substantially dissolve the mixture in the liquid medium. The dissolved mixture (i.e., substantially or completely dissolved mixture) may then be used in other inventive processes of the present invention, including processes for the conversion of carbohydrates to hydrocarbons, particularly non-aromatic and aromatic gasoline boiling range hydrocarbons.

In another embodiment of the present invention, a process is provided for converting carbohydrates to hydrocarbons which includes contacting a polysaccharide with an ion-exchange resin in a liquid medium under a condition to substantially dissolve the polysaccharide in the liquid medium to form a mixture. The mixture (i.e., substantially or completely dissolved mixture) is then contacted with a hydrogenation catalyst under a condition (i.e., reaction or conversion condition) sufficient to form a hydrogenated product. The hydrogenated product may then be contacted with a catalyst composition under a condition (i.e., reaction or conversion condition) sufficient to form a reaction product containing gasoline boiling range hydrocarbons.

In another embodiment of the present invention, a process is provided for converting carbohydrates to hydrocarbons which includes contacting an aqueous solution containing at least one carbohydrate with a hydrogenation catalyst under a condition sufficient to form a hydrogenated product. The hydrogenated product may then be contacted with a catalyst composition under a condition (i.e., reaction or conversion condition) sufficient to form a reaction product containing gasoline boiling range hydrocarbons.

Other objects, advantages and embodiments of the invention will be apparent from the following detailed description of the invention and the appended claims.

DETAILED DESCRIPTION OF THE INVENTION

Carbohydrates, such as starches and sugars may be converted in accordance with the present invention to form a hydrocarbon mixture useful for liquid fuels and chemicals. The term, "carbohydrate" is used generally to refer to a compound of carbon, hydrogen and oxygen having the general formula $C_x(H_2O)_y$, in which the ratio of hydrogen to oxygen is the same as in water. Carbohydrates include monosaccharides, polysaccharides, and mixtures of monosaccharides and/or polysaccharides. The term "monosaccharide" or "monosaccharides" are generally hydroxy aldehydes or hydroxy ketones which cannot be hydrolyzed into any simpler carbohydrate. Examples of monosaccharides include dextrose, glucose, fructose and galactose. The term "polysaccharide" or "polysaccharides" include those saccharides containing more than one monosaccharide unit. This term also includes disaccharides (such as sucrose, maltose, cellobiose, and lactose) and oligosaccharides.

Generally, carbohydrates useful in the present invention are characterized as having an overall effective hydrogen to carbon ratio of about zero, although carbohydrates having an overall effective hydrogen to carbon ratio greater than zero may also be used. The effective hydrogen to carbon ratio may be determined by the gross composition of the carbohydrate starting material according to the formula described in U.S. Pat. No. 4,503,278 of:

$$(H/C)_{eff}=(H-2(O)-3N-N-2S)/C$$

where H, C, O, N, and S are the relative atom ratios of hydrogen, carbon, oxygen, nitrogen and sulfur as determined by elemental analysis on an anhydrous basis. For example, the approximate chemical formula for starch is $(C_6H_{10}O_5)_n$. Inserting the appropriate values in the above equation gives:

$$H/C_{eff}=(10-2(5)-3(0)-0-2(0))/10=0/10=0.$$

Useful carbohydrates in the present invention include, but are not limited to, carbohydrates that can be converted to hydrocarbons when contacted under suitable reaction conditions. The carbohydrate starting material may be insoluble in an aqueous medium such as water, substantially insoluble in an aqueous medium, or partially insoluble in an aqueous medium. In addition, carbohydrates useful in the present invention may be soluble in an aqueous medium, substantially soluble in an aqueous medium, or partially soluble in an aqueous medium. In addition, carbohydrates useful in the present invention may be in a pure form, or may be mixed with other components, including but not limited to, additives. Examples of carbohydrates useful as starting materials in accordance with the present invention include, but are not limited to, polysaccharides such as sucrose, maltose, lactose, cellobiose, melibiose raffininose, starch (e.g., corn starch or other starches derived from other cereal grains such as wheat and rice, or those from tubers, such as potato, tapioca, and arrowroot, or those that are waxy starches such as waxy moil, maize and rice) and starch decomposition products such as dextrin and corn syrup (also known as glucose syrup).

In one embodiment of the present invention, insoluble starch (e.g., cornstarch) is used as the starting material. Starch, in its native form, is insoluble in water. Cornstarch may be found, for example, within corn kernels as a long polymer polysaccharide composed of two structural classes: amylose and amylopectin. Amylose, which is about 25% of the cornstarch, is water soluble while amylopectin, which is about 75% of the cornstarch, is insoluble.

In another embodiment of the present invention, corn syrup (sometimes referred to as glucose syrup) is used as the starting material. Corn syrup generally is a mixture of glucose, maltose, and maltodextrins and produced by the acid hydrolysis of starch. Generally, in the production of corn syrup, the starch source (e.g., corn) is suspended in water and liquefied in the presence of acid and/or enzymes that convert the starch first, to a mixture of glucose, maltose, and higher saccharides. Throughout the process, the processor may halt the actions of the acid or enzyme to produce the proper mixture of sugars for syrups to meet different needs. The degree of conversion of the starch varies, with a consequent effect on the dextrose equivalent (D.E.) or reducing power of the syrup. Thus, corn syrups generally have a range of molecular compositions, rather than a specific molecular composition.

In one embodiment of the present invention, carbohydrates may optionally be first hydrolyzed in a liquid medium such as water. It is understood that carbohydrates may not need to be hydrolyzed, as the carbohydrate or carbohydrate-containing material may be in a suitable aqueous form for processing and for converting the carbohydrate to a hydrocarbon product. In one embodiment of the present invention, the solubility of a carbohydrate, such as for example a polysaccharide such as starch, in a liquid medium may be increased by contacting the carbohydrate with an ion-exchange resin under a condition sufficient to partially, substantially, or completely, dissolve the carbohydrate in the liquid medium. In another embodiment of the present invention, the solubility of the carbohydrate in a liquid medium may be increased by contacting a carbohydrate with an ion-exchange resin in a liquid medium to form a mixture, and heating the mixture at a temperature sufficient to partially, substantially, or completely dissolve the mixture in the liquid medium.

The amount of carbohydrate used as the starting material in the present invention will vary depending on the size of the commercial process or suitability of the mixing/reaction vessel. Generally, when combined with water or other liquid at elevated temperatures, carbohydrates such as starch granules absorb water and swell to many times their original size thus making the gelatinized or swollen product very viscous. For example, when starch is used as a starting material in a solid form, the starch may contain in the range of from about 10 to about 90% solid particle, in relation to the percentage of liquid medium. In one embodiment of the present invention, the carbohydrate/liquid medium ratio is the range of from about 10 to about 80 weight percent, based on the total weight of the carbohydrate/liquid medium mixture. In another embodiment of the present invention, the carbohydrate/liquid medium ratio is the range of from about 15 to about 70 weight percent, based on the total weight of the carbohydrate/liquid medium mixture. In another embodiment of the present invention, the carbohydrate/liquid medium ratio is the range of from about 20 to about 60 weight percent, based on the total weight of the carbohydrate/liquid medium mixture.

Ion-exchange resins useful in the present invention generally are insoluble matrices (or support structures) of electrolytes normally in the form of small (1-2 mm diameter) beads, fabricated from an organic polymer substrate (such as polystyrene). In addition, the ion-exchange resins contain two types of ions, those which are bound within the substrate, and the oppositely charged counter ions that are free. When an ion-exchange resin is immersed in a medium in which it is insoluble or partially or substantially insoluble, the counter ions are mobile and may be exchanged for other counter ions from the surrounding medium, whereas ions of the same type of charge as the bound ions do not have free movement into and out of the polymer substrate. Generally, ion exchange resins useful in the present invention may be classified based on the charge of the exchangeable counter ion (cation exchanger or anion exchanger) and the ionic strength of the bound ion (strong exchanger or weak exchanger). Ion-exchange resins useful in the present invention may include by way of example strong cation-exchange resins or strongly acidic cation-exchange resins such as those containing sulfonic acid groups or corresponding salts. In addition, ion-exchange resins useful in the present invention may include by way of example weak cation-exchange resins or weakly acidic cation-exchange resins, such as those containing carboxylic acid groups or corresponding salts. In addition, ion exchange resins useful in the present invention may contain or be supported on various polymer substrates including, but not limited to, styrene, polystyrene, and acrylic-based monomers.

Non-limiting suitable examples of ion-exchange resins useful in the present invention, include but are not limited to, Amberlyst™-15, Amberlyst™ XN-1005, Amberlyst™ XN-1008, Amberlyst™ XN-1010, Amberlyst™ XN-1011, Amberlite™ 200, Amberlite™-IR-120 (H), and combinations thereof. In one embodiment of the present invention, the ion-exchange resin is a polystyrene supported resin containing sulfonic acid groups commercially available from Rohm and Haas under the trade designation "Amberlite™ IR-120 (H)."

Generally, ion exchange resins useful in the present invention are present in an amount in the range of from about 0.02 to about 10 percent, based on the weight of the carbohydrate/liquid medium mixture. In one embodiment of the present invention, the ion exchange resin is present in an amount in the range of from about 0.04 to about 4 percent, based on the weight of the carbohydrate/liquid medium mixture. In another embodiment of the present invention, the ion exchange resin is present in an amount in the range of from about 0.06 to about 2 percent, based on the weight of the carbohydrate/liquid medium mixture. In another embodiment of the present invention, the ion exchange resin is present in an amount in the range of from about 0.08 to about 1 percent, based on the weight of the carbohydrate/liquid medium mixture.

Carbohydrates useful in the present invention may be dissolved in any aqueous reaction medium, including water. In addition reaction of carbohydrates with ion-exchange resins in accordance with the present invention may be carried out in any suitable type of apparatus which enable intimate contact of the reactants and control of the operating conditions. The process may be carried out in batch, semi-continuous, or continuous operation. In one embodiment of the present invention, a batch operation in a conventional autoclave is used.

In one embodiment of the present invention, the carbohydrate/liquid medium/ion-exchange resin mixture may be loaded in a sufficient amount in an autoclave and the system flushed with nitrogen or other suitable gas and sealed. In one embodiment of the present invention, the mixture may be contacted under a condition sufficient to produce a partially dissolved mixture, substantially dissolved mixture, or completely dissolved mixture. Generally, such a condition may include heating the mixture for a time period in the range of from about 10 minutes to about 50 minutes at a temperature in the range of from about 80° C. to about 300° C., and a pressure in the range of from about 10 to about 100 psig. It is, however, understood that higher and lower temperatures and pressures than those described above may be used when deemed necessary or desirable to optimize results.

In one embodiment of the present invention, the carbohydrate/liquid medium/ion-exchange resin mixture is heated at a temperature is in the range of from about 50° C. to about 250° C. In another embodiment of the present invention, the temperature is in the range of from about 100° C. to about 200° C. In another embodiment of the present invention, the temperature is in the range of from about 110° C. to about 150° C. In another embodiment of the present invention, the carbohydrate/liquid medium/ion exchange resin mixture is subjected to a pressure is in the range of from about 0 to about 500 psig. In another embodiment of the present invention, the pressure is in the range of from about 10 to about 250 psig. In another embodiment of the present invention, the pressure is in the range of from about 15 to about 100 psig. In one embodiment of the present invention, the carbohydrate/liquid medium/ion-exchange resin mixture is subjected to a temperature and pressure for a time period in the range of from about 10 minutes to about 120 minutes. In another embodiment of the present invention, the time period is in the range of from about 20 minutes to about 90 minutes. In still another embodiment of the present invention, the time period is in the range of from about 25 minutes to about 60 minutes.

In one embodiment of the present invention, the carbohydrate/liquid medium/ion exchange resin mixture is heated to a temperature of approximately 140° C. and held for 30 minutes. In one embodiment of the present invention, the carbohydrate/liquid medium/ion exchange resin mixture is not subjected to additional pressure, other than the natural pressure resulting from heating that carbohydrate/liquid medium/ion exchange resin mixture.

Generally, the carbohydrate-containing starting material, after being contacted with a suitable ion-exchange resin under a sufficient condition, produces a partially dissolved, substantially dissolved, or completely dissolved, carbohydrate starting material in the liquid medium. In one embodiment of the present invention, 100% of the carbohydrate is dissolved in the aqueous medium. In another embodiment of the present invention, greater than 95 percent of the carbohydrate is dissolved in the aqueous medium. In addition, approximately 50-80% of the carbohydrate starting material (for example, polysaccharides) may be converted to its basic monosaccharide, as a result of the hydrolysis in the present of an ion-exchange resin, as measured by dextrose equivalents tests.

In accordance with the present invention, a hydrolyzed, substantially hydrolyzed, or completely hydrolyzed carbohydrate-containing product may optionally thereafter be hydrogenated by contacting the hydrolyzed, substantially hydrolyzed, or completely hydrolyzed carbohydrate-containing product with either hydrogen or hydrogen mixed with a suitable gas along with a catalyst composition under a condition sufficient to form a hydrogenated product. In addition, in accordance with the present invention, a non-hydrolyzed carbohydrate-containing material may be hydrogenated by contacting the non-hydrolyzed carbohydrate-containing material with hydrogen or other suitable gas along with a catalyst composition under a condition sufficient to form a hydrogenated product.

Generally, suitable hydrolyzed, substantially hydrolyzed, or completely hydrolyzed carbohydrate-containing materials and/or non-hydrolyzed carbohydrate-containing materials include, but are not limited to, materials containing polysaccharides and/or monosaccharides, such as for example, dextrose, mannose, galactose, fructose and sucrose, and products derived from hydrolyzed polysaccharides such as starch. Other suitable carbohydrate-containing materials, include, but are not limited to, corn syrup and related products. Generally, any oxygenated hydrocarbon molecule may used in the present inventive process.

Useful catalysts in the present invention include catalysts used to produce a hydrogenated product in the conversion of carbohydrates to hydrocarbons. Generally, hydrogenation catalysts useful in the present invention include those containing an active metal on a support material. Examples of suitable metals include, but are not limited to, platinum, palladium, nickel, copper, iron, cobalt, zinc, lead, tin, mercury, ruthenium, combinations thereof, metal alloys of such metals, and oxides and chlorides of such metals.

The metal of the hydrogenation catalyst useful in the present invention is usually distributed over the surface of a support in a manner than maximizes the surface area of the metal. Examples of suitable support materials for the hydrogenation catalysts include, but are not limited to, silica, silica-alumina, aluminum oxide ($Al_2O_3$), silica-magnesia, silica-titania and acidic zeolites of natural or synthetic origin. The metal catalyst may be prepared by any method known in the art, including combining the metal with the support using conventional means including but not limited to impregnation, ion exchange and vapor deposition. In one embodiment of the present invention, the catalyst contains ruthenium supported on alumina. In another embodiment of the present invention, the catalyst contains ruthenium supported on an ion-exchange resin (such as for example, Amberlite™ 120 (H) commercially available from Rohm and Haas). Generally, the use of an ion-exchange resin as the support may allow the conversion of a generally non-hydrolyzed carbohydrate-containing compound (such as for example, starch) to be hydrolyzed and hydrogenated in one step by contacting the non-hydrolyzed carbohydrate-containing compound with a ruthenium/ion-exchange resin catalyst under a condition sufficient to form a hydrolyzed/hydrogenated product.

The hydrogenation catalyst employed in the present invention may vary over a wide range and will depend upon the particular catalyst, carbohydrate, temperature and pressure which are employed in the process.

Reaction, or conversion, conditions for contacting a hydrolyzed, substantially hydrolyzed, or completely hydrolyzed carbohydrate-containing material and/or non-hydrolyzed carbohydrate-containing material includes a reaction temperature in the range of from about 80° C. to about 300° C. In another embodiment of the present invention, the temperature is in the range of from about 90° C. to about 250° C. In another embodiment of the present invention, the temperature is in the range of from about 100° C. to about 200° C. In another embodiment of the present invention, the temperature is in the range of from about 110° C. to about 180° C.

The reaction, or conversion, conditions for contacting a hydrolyzed, substantially hydrolyzed, or completely hydrolyzed carbohydrate-containing material and/or non-hydrolyzed carbohydrate-containing material includes a pressure in the range of from about 100 pounds per square inch gauge (psig) to about 2000 psig. In one embodiment of the present invention, the pressure is in the range of from about 550 to about 1900 psig. In another embodiment of the present invention, the pressure is in the range of from about 600 to about 1800 psig. In still another embodiment of the present invention, the pressure is in the range of from about 650 to about 1700 psig.

The carbohydrate-containing material may be contacted with a suitable gas, such as for example, hydrogen, in order to form a hydrogenated product. The gas may be introduced into the reaction chamber under pressure, which may vary with the nature of the reactants and the hydrogenation catalyst employed. The rate at which gas is charged to the reaction vessel is any suitable rate.

The time of reaction will depend upon the specific starting material, concentration, the specific catalyst used, pressure and temperature. Generally, the duration of reaction is in the range of from about 20 minutes to about 120 minutes, which may be shorter or longer depending on the desired hydrogenation. The reaction is carried out in any suitable type of apparatus or reaction chamber which enable intimate contact of the reactants and control of the operating conditions. The process may be carried out in batch, semi-continuous, or continuous operation. In one embodiment of the present invention, a batch operation in a conventional autoclave is used. The reactants may be added to the reaction chamber in any suitable manner or in any suitable order. In one embodiment of the present invention, the hydrogenation catalyst is added first to the carbohydrate-containing solution, and thereafter, fed with hydrogen.

Liquid product from the hydrogenation step is believed to contain, among other things, polyhydric alcohols of the respective monosaccharide sugar. For example, when corn-starch (whose basic structural components consist of glucose units), is hydrolyzed and hydrogenated, the resulting reaction product contains the polyhydric alcohol-sorbitol.

In accordance with the present invention, a hydrogenated carbohydrate-containing product may be contacted with a suitable zeolite catalyst composition under a condition sufficient to produce a reaction product containing gasoline boiling range hydrocarbons. In addition, in accordance with the present invention, a non-hydrogenated carbohydrate-containing material may be contacted with a suitable zeolite catalyst composition under a condition sufficient to produce a reaction product containing gasoline boiling range hydrocarbons. In accordance with the present invention, a hydrogenated carbohydrate-containing product, or a non-hydrogenated carbohydrate-containing product, or mixtures thereof, may be combined with an additional alkane, such as for example, iso-pentane, and thereafter, contacted with a suitable zeolite catalyst composition under a condition sufficient to produce a reaction product containing gasoline boiling range hydrocarbons.

Generally, suitable hydrogenated carbohydrate-containing products, or non-hydrogenated carbohydrate-containing products, or mixtures thereof, useful in the present invention, include but are not limited to, carbohydrate-containing materials that are hydrolyzed, substantially hydrolyzed, or completely hydrolyzed, and those that have not been hydrolyzed. In addition, suitable hydrogenated carbohydrate-containing products, or non-hydrogenated carbohydrate-containing products, or mixtures thereof, useful in the present invention, include, but are not limited to, materials containing polysaccharides and/or monosaccharides, such as for example, dextrose, mannose, galactose, fructose and sucrose, and products derived from hydrolyzed polysaccharides such a starch. Other suitable carbohydrate-containing materials, include, but are not limited to, corn syrup and related products, as well as oxygenated hydrocarbon compounds, such as for example, lactic acid and sorbitol.

Carbohydrate-containing products, which may be hydrolyzed, hydrogenated, or both hydrolyzed and hydrogenated, or not hydrolyzed or hydrogenated, may be contacted with a catalyst composition containing a zeolite under a condition sufficient to produce a reaction product containing gasoline boiling range hydrocarbons. Useful catalyst compositions in the present invention include zeolites or zeolite material effective in the conversion of carbohydrates to hydrocarbons when contacted under suitable reaction conditions. Examples of suitable zeolites include, but are not limited to, those disclosed in Kirk-Othmer Encyclopedia of Chemical Technology, third edition, volume 15, pages 638-669 John Wiley & Sons, New York, 1981). Generally, zeolites useful in the present invention have a constraint index (as defined in U.S. Pat. No. 4,097,367, which is incorporated herein by reference) in the range of from about 0.4 to about 12, and preferably in the range of from about 2 to about 9. In addition, the molar ration of $SiO_2$ to $Al_2O_3$ in the crystalline framework of the zeolite is at least about 5:1 and can range up to infinity. In one embodiment of the present invention, the molar ratio of $SiO_2$ to $Al_2O_3$ in the crystalline framework of the zeolite is in the range of from about 8:1 to about 200:1. In another embodiment of the present invention, $SiO_2$ to $Al_2O_3$ in the crystalline framework of the zeolite is in the range of from about 12:1 to about 100:1. Zeolites useful in the present invention include but are not limited to ZSM-5, ZSM-8, ZSM-11, ZSM-12, ZSM-35, ZSM-38 and combinations thereof. Some of these zeolites are also known as "MFI" or "Pentasil" zeolites. In one embodiment of the present invention, the zeolite is ZSM-5. Modified zeolites can also be used. Modified zeolites can include zeolites modified by metal cations, such as, for example, zinc, gallium, or nickel. Zeolites can also be modified by steam treatment and/or acid treatment. In addition, zeolites of the present invention may be combined with a clay, promoter, and/or a binder. Zeolites useful in the present invention may also contain an inorganic binder (also referred to as matrix material) selected from the group consisting of alumina, silica, alumina-silica, aluminum phosphate, clays (such as bentonite), and combinations thereof. The type of zeolite used will cause the final product to vary considerably.

Reaction, or conversion, conditions for contacting a carbohydrate-containing material, whether or not such material has been hydrolyzed and/or hydrogenated, includes a reaction temperature in the range of from about 100° C. to about 1000° C. In another embodiment of the present invention, the temperature is in the range of from about 150° C. to about 800° C. In another embodiment of the present invention, the temperature is in the range of from about 200° C. to about 600° C. In another embodiment of the present invention, the temperature is in the range of from about 300° C. to about 500° C. The reaction, or conversion, conditions for contacting a carbohydrate-containing material, whether or not such material has been hydrolyzed and/or hydrogenated, includes a pressure in the range of from about 1 pound per square inch gauge (psig) to about 500 pounds per square inch gauge (psig). In one embodiment of the present invention, the pressure is in the range of from about 3 to about 400 psig. In another embodiment of the present invention, the pressure is in the range of from about 5 to about 200 psig.

The carbohydrate-containing material, whether or not such material has been hydrolyzed and/or hydrogenated, may be contacted with a suitable gas, such as for example, hydrogen or nitrogen in order to form a product containing hydrocarbons. The gas may be introduced into the reaction chamber under pressure, which may very with the nature of the reactants and the zeolite catalyst employed. The flow rate may vary depending on the specific reaction conditions. In one embodiment of the present invention, the flow rate of gas is approximately in the range of 25 cc/min to 300 cc/min.

The time of reaction will depend upon the specific starting material, concentration, the specific catalyst used, pressure and temperature. Generally, the duration of reaction is in the range of from about 0.01 to about 100 minutes, which may be shorter or longer depending on the desired hydrogenation. The reaction is carried out in any suitable type of apparatus or reaction chamber which enable intimate contact of the reactants and control of the operating conditions. The process may be carried out in batch, semi-continuous, or continuous operation. In one embodiment of the present invention, a batch operation in a conventional autoclave is used. The reactants may be added to the reaction chamber in any suitable manner or in any suitable order. In one embodiment of the present invention, the carbohydrate-containing solution is fed through the zeolite catalyst.

The process effluent, from the conversion zone, in accordance with the present invention, generally may contain gas and liquid fractions containing hydrocarbon products, which include, but are not limited to, a light gas fraction containing hydrogen, and methane, a $C_2$-$C_3$ fraction containing ethane, propane, ethylene, and propylene, an intermediate fraction including non-aromatic compounds having greater than 3 carbon atoms, a BTX aromatic hydrocarbons fraction (containing benzene, toluene, ortho-xylene, meta-xylene, and para-xylene) and a $C_9$-$C_{13}$+ fraction containing aromatic compounds having 9-13 or more carbon atoms per molecule.

In addition, the process effluent of the present invention, may also contain by products of carbon monoxide and carbon dioxide ($CO_x$). According to one embodiment of the present invention, the hydrocarbon product contain less $CO_x$, and less coke and other undesirable products are produced, when the reaction conditions are modified, for example, when the reaction conditions are at pressures generally in the range of from about 100 psig to about 200 psig. In addition, it has been discovered that higher reaction pressures, preferably at about 200 psig, result in the production of less $CO_x$ (preferably less than about 25 weight percent of the product), less coke, and upgrading of the hydrocarbon stream to a higher-octane gasoline.

The following examples are presented to further illustrate the present invention and are not to be construed as unduly limiting the scope of this invention.

EXAMPLE I

This example illustrates the increased solubility of starting carbohydrate materials, such as for example, polysaccharides such as starch, when treated with ion-exchange resins in accordance with the present invention.

Run 1 (Control)

As shown in Table I-A below, a 40.02 gram sample of solid corn starch (commercially available from retail sources) was mixed with 100 mL of water by stirring. The starch/water solution was loaded to 300 cc in an autoclave, and the system was flushed with nitrogen and sealed. The mixture was then heated to 140° C. at about 50 psig and held for approximately 30 minutes while stirring. The mixture was then allowed to cool to room temperature and the mixture was discharged from the autoclave. It was observed that the corn starch in Run 1 did not dissolve in water after heating.

Run 2 (Control)

As shown in Table I-A, a 40.02 gram sample of solid corn starch (commercially available from retail sources) was mixed with 100 mL of carbonated water (from club soda). The starch/club soda solution was loaded to 300 cc in an autoclave, and the system was flushed with nitrogen and sealed. The mixture was then heated to 140° C. at about 50 psig and held for approximately 30 minutes while stirring. The mixture was then allowed to cool and the mixture was discharged from the autoclave. It was observed that the corn starch in Run 2 did not dissolve in slightly acidified water after heating.

Run 3 (Invention)

As shown in Table I-A, a 40.02 gram sample of corn starch (commercially available from retail sources) was added to 100 mL water, along with 1.0 gram of Amberlite™ IR-120(H) (commercially available from Rohm and Haas) and was mixed by stirring. The corn starch/water/Amberlite™ mixture was loaded into an autoclave and flushed with nitrogen and sealed, and thereafter was heated to approximately 140° C. at about 50 psig and held for approximately 30 minutes while stirring. After cooling down and discharging the materials from the autoclave, it was observed that 100% of the corn starch dissolved in water. Dextrose Equivalence tests (DE) were run after treatment to measure the extent of hydrolysis. The DE results suggested that about 50 to about 80 percent of the corn starch was converted to the monosaccharide sugar dextrose after heating in the presence of the ion exchange resin.

TABLE II-A

Carbohydrate Dissolution

| Step | Carbohydrate | Liquid medium | Temperature/ Pressure | Ion Exchange Resin | Resulting product |
|---|---|---|---|---|---|
| 1 | Starch (40.02 g) | Water (100 mL) | 140° C./ 50 psig* | Amberlite ™ IR-120(H) (1 g) | Liquid; 100% of starch dissolved |

*Note -
autoclave was not pressurized before heating; pressure increase is due to vapor pressure of water at heated temperature.

Step 2—Hydrogenation

The liquid product from step 1, along with hydrogen gas, was fed through a Ru/Al$_2$O$_3$ catalyst at 140° C. and 150 psig as shown in Table II-B below:

TABLE II-B

Hydrogenation

| Step | Gas Feed | Liquid Feed | Temperature/ Pressure | Hydrogenation Catalyst | Resulting product |
|---|---|---|---|---|---|
| 2 | Hydrogen (300 cc/min) | liquid product from step 1 (15 cc/hour) | 140° C./ 150 psig | Ru/Al$_2$O$_3$ | Liquid |

TABLE I-A

Carbohydrate Dissolution

| Run | Carbohydrate | Liquid medium | Temperature/ Pressure | Ion Exchange Resin | Results |
|---|---|---|---|---|---|
| 1 (control) | Starch (40.02 g) | Water (100 mL) | 140° C./50 psig* | None | Starch did not completely dissolve; solid/liquid product |
| 2 (control) | Starch (40.02 g) | Club Soda (100 mL) | 140° C./50 psig* | None | Starch did not completely dissolve; solid/liquid product |
| 3 (invention) | Starch (40.02 g) | Water (100 mL) | 140° C./50 psig* | Amberlite ™ IR-120(H)(1 g) | 100% of starch dissolved Liquid product |

*Note -
autoclave was not pressurized before heating; pressure increase was due to vapor pressure of liquid at heated temperature.

EXAMPLE II

This example illustrates a process of converting carbohydrates to gasoline boiling range hydrocarbons (such as for non-aromatic and aromatic gasoline boiling range hydrocarbons) including hydrolyzing the carbohydrate-containing product, hydrogenating the product, and then converting the product over a zeolite catalyst.

Step 1—Dissolution

Run 3 from Example I was repeated two (2) additional times, and the liquid product from all three (3) runs was pooled together, as shown in Table II-A below.

The hydrogenated liquid product was collected and used for the liquid feed in step 3 below.

Step 3—Reaction of Product Over ZSM-5

The hydrogenated liquid product from Step 2 was collected and used as feed, and reacted over ZSM-5 catalyst as shown in Table II-C below. Both the gas phase and liquid phase products were analyzed to determine the hydrocarbon product distribution.

TABLE II-C reaction of product over ZSM-5

| Step | Gas Feed | Liquid Feed | Temperature/ Pressure | Second Catalyst | Resulting product |
|---|---|---|---|---|---|
| 3 | n/a | liquid product from step 2 (26 cc/hour) | 400° C./ 10 psig | ZSM-5 (8.0 g) | *See product distribution in Table II-D and Table II-E |

TABLE II-D

Hydrocarbon product distribution (includes both gas and liquid phase)

| | Carbon Number | | | | | | | |
|---|---|---|---|---|---|---|---|---|
| | C1 | C2= | C2 | C3= | C3 | C4= | C4 | C5+ |
| Weight Percent | 0.35 | 3.71 | .020 | 7.59 | .032 | 2.58 | 0.98 | 84.27 |

TABLE II-E

Liquid Phase Hydrocarbon Product Analyzed by DHA method

| Carbon Number/Group | Weight percent |
|---|---|
| C5 | 0.021 |
| C6 | 0.366 |
| C7 | 5.096 |
| C8 | 17.353 |
| C9 | 15.014 |
| C10 | 15.756 |
| C11 | 9.123 |
| C12 | 3.997 |
| C13+ | 12.215 |
| Aromatics | 58.499 |
| Paraffin | 0.708 |
| i-Paraffin | 4.994 |
| Naphthenes | 1.177 |
| Unidentified | 21.059 |
| Plus | 12.157 |
| Olefins | 1.406 |

EXAMPLE III

This example illustrates a process of converting corn syrup to gasoline boiling range hydrocarbons (such as for non-aromatic and aromatic gasoline boiling range hydrocarbons) including hydrogenating the corn syrup, and then converting the product over a zeolite catalyst.

Step 1—Hydrogenation of Corn Syrup

A corn syrup/water (50 wt %/50 wt %) solution and hydrogen gas were fed through a Ru/Al$_2$O$_3$ catalyst at 200° F. and 150 psig as shown in Table III-A below:

TABLE III-A

Hydrogenation of Corn Syrup

| Step | Gas Feed | Corn Syrup/Water Feed | Temperature/ Pressure | First Catalyst | Resulting product |
|---|---|---|---|---|---|
| 1 | Hydrogen (300 cc/min) | Corn Syrup/Water Feed (50 wt %/50 wt %) (13.13 cc/hr) | 200° F./ 150 psig | Ru/ Al$_2$O$_3$ | Liquid |

The hydrogenated liquid product was collected and used for the liquid feed in step 2 below.

Step 2—Conversion Over ZSM-5

The hydrogenated liquid product was collected and used as feed, and reacted over ZSM-5 catalyst as shown in the table below. Both the gas phase and liquid phase products were analyzed by gas chromatography to determine the hydrocarbon product distribution.

| Step | Gas Feed | Liquid Feed | Temperature/ Pressure | Second Catalyst | Resulting product |
|---|---|---|---|---|---|
| 2 | n/a | Product from Step 1 (24 cc/hour) | 400° C./ 10 psig | 8.0 g ZSM-5 | *See product distribution in Table III-B and Table III-C below |

TABLE III-B

Hydrocarbon product distribution (includes both gas and liquid phase)

| | Carbon Number | | | | | | | |
|---|---|---|---|---|---|---|---|---|
| | C1 | C2= | C2 | C3= | C3 | C4= | C4 | C5+ |
| Weight Percent | 0.15 | 3.01 | 0.1 | 4.43 | 0.35 | 1.52 | 0.25 | 90.19 |

TABLE III-C

Liquid Phase Hydrocarbon Product Analyzed by DHA method

| Carbon Number/Group | Weight percent |
|---|---|
| C5 | 0.019 |
| C6 | 0.932 |
| C7 | 10.098 |
| C8 | 23.377 |
| C9 | 14.71 |
| C10 | 12.764 |
| C11 | 9.045 |
| C12 | 3.161 |
| C13+ | 6.815 |
| Aromatics | 69.52 |
| Paraffin | 0.36 |
| i-Paraffin | 2.66 |
| Naphthenes | 0.77 |
| Unidentified | 19.08 |
| Plus | 6.77 |
| Olefins | 0.85 |

EXAMPLE IV

This example illustrates a process of converting hydrogenated carbohydrates, specifically, sorbitol, to gasoline boiling range hydrocarbons (such as for non-aromatic and aromatic gasoline boiling range hydrocarbons) by combining sorbitol with iso-pentane, and reacting the mixture over ZSM-5 catalyst.

In this example, a sorbitol/water/iso-pentane mixture was co-fed along with hydrogen gas through a ZSM-5 zeolite. As shown in the Table IV-A, conversions of sorbitol and iso-pentane were observed. The liquid product was rich in aromatics and the gas phase product was rich in olefins. About 28 weight percent of the product was C$_2$-C$_4$ olefins, 16 weight percent $CO_x$, 51 weight percent $C_5+$ and 5 weight percent $C_1$-$C_4$ paraffins. For the liquid product, about 83% were aromatics with most being $C_7$ or $C_8$.

TABLE IV-A

Sorbitol + Iso-pentane

| Feed 1 HC-liquid | Feed 2 | Gas Feed | Temp. | Catalyst | Resulting product |
|---|---|---|---|---|---|
| I-C5 (density - .62 g/mL) | Sorbitol (28.6 wt %) Water (71.4 wt %) density (1.103 g/mL) | H2 (150 mL/min) | 500° C. | 8.0 g ZSM-5 | *See product distribution in Table IV-B, Table IV-C, and Table IV-D below. |

TABLE IV-B

Reactant % Conversion

| Reactant | % Conversion |
|---|---|
| Sorbitol | 95.93 |
| I-C5 | 19.41 |

TABLE IV-C

Liquid Phase Hydrocarbon Product Analyzed by DHA method

| Carbon Number/Group | Weight percent |
|---|---|
| C4 | 0.3 |
| C5 | 1.7 |
| C6 | 6.4 |
| C7 | 25.4 |
| C8 | 30.6 |
| C9 | 8.2 |
| C10 | 9.8 |
| C11 | 6.0 |
| C12+ | 4.1 |
| Aromatics | 83.1 |
| Paraffin | 0.5 |
| i-Paraffin | 2.1 |
| Naphthenes | 0.7 |
| Unidentified | 7.5 |
| Plus | 2.9 |
| Olefins | 3.3 |

TABLE IV-D

Product selectivity

| Group | Carbon mole % |
|---|---|
| C1–C4 paraffins | 5.0 |
| C2–C4 olefins | 28.4 |
| C5+ | 50.6 |
| $CO_x$ | 16.0 |

EXAMPLE V

This example illustrates the effect of pressure on the hydrocarbon product stream resulting from the conversion of carbohydrates to gasoline boiling range hydrocarbons (such as for non-aromatic and aromatic gasoline boiling range hydrocarbons). As shown in Table V-A below, with the increase in reaction pressure, the conversion of sorbitol (used in this example) was 99 weight percent. With an increase in pressure, there was an increase in $C_1$-$C_4$ paraffins, a decrease in $C_2$-$C_4$ olefins, a decrease in coke, and increase in $C_5+$, and a decrease in the amount of sorbitol carbon converted to $CO_x$. In addition, Table V-A shows that at higher pressures, more of the oxygen in sorbitol is removed as water with iso-pentane acting as the hydrogen donor. In addition to reducing the $CO_x$ yield from sorbitol, higher pressures result in upgrading of iso-pentane to a higher-octane gasoline.

TABLE V

Effect of reaction pressure on hydrocarbon product

| | Run | | |
|---|---|---|---|
| | 1 | 2 | 3 |
| Pressure, psig | 20 | 100 | 200 |
| Temperature, ° C. | 500 | 500 | 500 |
| N2 flow rate, mL/min. | 25 | 125 | 250 |
| Catalyst | ZSM-5 | ZSM-5 | ZSM-5 |
| Feed I (11 mL/hr) | Sorbitol/H$_2$O (50:50) | Sorbitol/H$_2$O (50:50) | Sorbitol/H$_2$O (50:50) |
| Feed II (6.5 mL/hr) | IC-5 | IC-5 | IC-5 |
| Sorbitol conversion % | 99.0 | 99.0 | 99.0 |
| I-C-5 conversion % | 26.0 | 55.1 | 55.0 |
| Product distribution C mole % per run | | | |
| C1–C4 paraffins | 5.3 | 11.3 | 15.7 |
| C2–C4 olefins | 12.6 | 7.4 | 7.5 |
| C5+ | 53.1 | 59.9 | 59.9 |
| Coke | 7.3 | 5.1 | 4.9 |
| $CO_x$ | 21.7 | 16.3 | 12.0 |
| Sorbitol C to $CO_x$ % | 29.2 | 28.0 | 20.8 |

EXAMPLE VI

This example illustrates a process of converting oxygen-containing hydrocarbons, specifically, lactic acid, to gasoline boiling range hydrocarbons (such as for non-aromatic and aromatic gasoline boiling range hydrocarbons) using a ZSM-5 catalyst.

In this example, lactic acid was converted to gasoline range hydrocarbons and chemicals (light olefins) as shown in Table VI-A below. The lactic acid conversion was 78.7 percent with selectivity to $C_1$-$C_4$ paraffins, $C_2$-$C_4$ olefins, $C_5+$ hydrocarbons.

TABLE VI-A

Lactic Acid conversion

| Feed | Gas Feed | Temp. | Catalyst | Lactic Acid conversion (%) | Resulting product |
|---|---|---|---|---|---|
| 85% lactic acid in water (20 mL/hour) | N$_2$ (100 mL/min) | 500° C. | 6.0 g ZSM-5 | 78.7% | *See product distribution in Table VI-B below |

TABLE VI-B

Product selectivity

| Group | Carbon mole % |
|---|---|
| C1–C4 paraffins | 4.0 |
| C2–C4 olefins | 15.6 |

TABLE VI-B-continued

| | Product selectivity |
|---|---|
| Group | Carbon mole % |
| C5+ (mainly aromatics) | 42.5 |
| COx | 38.0 |

The results shown in the above examples, clearly demonstrate that the present invention is well adapted to carry out the objects and attain the ends and advantages mentioned as well as those inherent therein. Reasonable variations, modifications and adaptations may be made within the scope of this disclosure and the appended claims without departing from the scope of the invention.

What is claimed is:

1. A process comprising:
   contacting a carbohydrate-containing material with an ion-exchange resin in a liquid medium to form a mixture;
   heating said mixture at a temperature sufficient to substantially dissolve said carbohydrate-containing material in said liquid medium; and
   contacting said mixture with a hydrogenation catalyst under a condition sufficient to form a hydrogenated product.

2. The process of claim 1, wherein said carbohydrate-containing material has an effective hydrogen to carbon ratio of less than about one.

3. The process of claim 1, wherein said carbohydrate-containing material is a polysaccharide.

4. The process of claim 1, wherein said carbohydrate-containing material is selected from the group consisting of starch, cellulose, glycogen and mixtures thereof.

5. The process of claim 1, wherein said carbohydrate-containing material is starch.

6. The process of claim 1, wherein said ion-exchange resin comprises a strongly acidic cation-exchange resin.

7. The process of claim 1, wherein said ion-exchange resin contains sulfonic groups.

8. The process of claim 1, wherein said ion-exchange resin is present in an amount in the range of from about 0.02 to about 10 weight percent, based on the weight of the mixture.

9. The process of claim 1, wherein said temperature is in the range of from about 100.degree.C. to about 180.degree.C.

10. The process of claim 1, wherein said temperature is in the range of from about 120.degree.C. to about 160.degree.C.

11. The process of claim 1, wherein said temperature is in the range of from about 120.degree.C. to about 140.degree.C.

12. The process of claim 1, wherein said contacting comprises loading the mixture into an autoclave, flushing the autoclave with nitrogen, and sealing the autoclave.

13. The process of claim 1, wherein said heating comprises heating the mixture at a temperature in the range of from about 100.degree.C. to about 180.degree.C. until the mixture is dissolved.

14. The process of claim 1, wherein said liquid medium is water.

15. The process of claim 1, wherein said ion-exchange resin is a polystyrene supported resin containing sulfonic acid groups.

16. The process of claim 1, wherein between 95% and 100% of said carbohydrate-containing material is dissolved in said liquid medium.

17. A process comprising:
   contacting a carbohydrate-containing material with an ion-exchange resin in a liquid medium under a condition sufficient to substantially dissolve the carbohydrate-containing material in the liquid medium to form a mixture,
   contacting the mixture with a hydrogenation catalyst under a condition sufficient to form a hydrogenated product, and
   contacting a mixture comprising the hydrogenated product with a catalyst composition comprising a zeolite under a condition sufficient to form a reaction product containing gasoline boiling range hydrocarbons.

18. The process of claim 17, wherein said carbohydrate-containing material has an effective hydrogen to carbon ratio of less than about 1.

19. The process of claim 17, wherein said carbohydrate-containing material is a polysaccharide.

20. The process of claim 17, wherein said carbohydrate-containing material is selected from the group consisting of starch, cellulose, glycogen and mixtures thereof.

21. The process of claim 17, wherein said carbohydrate-containing material is starch.

22. The process of claim 17, wherein the ion-exchange resin comprises an acidic cation-exchange resin.

23. The process of claim 17, wherein the ion-exchange resin contains sulfonic groups.

24. The process of claim 17, wherein said ion-exchange resin is present in an amount in the range of from about 0.02 to about 10 weight percent, based on the weight of the mixture.

25. The process of claim 17, wherein said condition sufficient to substantially dissolve the carbohydrate-containing material in the liquid medium to form a mixture comprises a temperature in the range of from about 100.degree.C. to about 180.degree.C. and a pressure in the range of from about 10 to about 500 psig.

26. The process of claim 17, wherein said hydrogenation catalyst comprises a supported ruthenium catalyst.

27. The process of claim 17, wherein said condition sufficient to form a hydrogenated product comprises a temperature in the range of from about 80.degree. C. to about 300.degree.C. and a pressure in the range of from about 100 to about 2000 psig.

28. The process of claim 17, wherein said condition sufficient to form a reaction product containing gasoline boiling range hydrocarbons comprises a temperature in the range of about 200.degree.C. to about 800.degree.C. and a pressure in the range of from about 1 to about 500 psig.

29. The process of claim 17, wherein said contacting comprises loading the mixture into an autoclave, flushing the autoclave with nitrogen, and sealing the autoclave.

30. The process of claim 17, wherein said heating comprises heating the mixture at a temperature in the range of from about 100.degree.C. to about 180.degree.C. until the mixture is dissolved.

31. The process of claim 17, wherein said liquid medium is water.

32. The process of claim 17, wherein said ion-exchange resin is a polystyrene supported resin containing sulfonic acid groups.

33. The process of claim 17, wherein between 95% and 100% of said carbohydrate-containing material is dissolved in said liquid medium.

34. The process of claim 17, wherein said hydrogenated product is selected from the group consisting of ketones, epoxides, diols, glycols, furans, and organic acids.

35. The process of claim 17, wherein said hydrogenated product is lactic acid.

36. The process of claim 17, wherein said hydrogenated product is sorbitol.

37. The process of claim 17, wherein said mixture further comprises a hydrocarbon.

38. The process of claim 37, wherein said hydrocarbon is isopentane.

39. A process in accordance with claim 17 wherein said zeolite is selected from the group consisting of ZSM-5, ZSM-8, ZSM-11, ZSM-12, ZSM-35, ZSM-38 and combinations thereof.

40. A process in accordance with claim 17 wherein said zeolite is ZSM-5.

41. The process in accordance with claim 17 further comprising a step of modifying a zeolite by steam treatment prior to a step of contacting a mixture comprising the hydrogenated product with a catalyst composition comprising said zeolite.

42. The process in accordance with claim l7 further comprising a step of modifying a zeolite by acid treatment prior to a step of contacting a mixture comprising the hydrogenated product with a catalyst composition comprising said zeolite.

43. The process in accordance with claim 17 further comprising a step of modifying a zeolite by metal cation prior to a step of contacting a mixture comprising the hydrogenated product with a catalyst composition comprising said zeolite.

44. A process in accordance with claim 43 wherein said metal cation is selected from the group consisting of zinc, gallium, and nickel.

45. A process comprising:
contacting an aqueous solution containing at least one carbohydrate with a hydrogenation catalyst under a condition sufficient to form a hydrogenated product, and
contacting the hydrogenated product with a catalyst composition comprising a zeolite under conditions sufficient to form a reaction product containing gasoline boiling range hydrocarbons.

46. The process of claim 45, wherein the aqueous solution contains corn syrup.

47. The process of claim 45, wherein the hydrogenation catalyst comprises a supported ruthenium catalyst.

48. The process of claim 45, wherein the conditions sufficient to form a hydrogenated product comprises a temperature n the range of from about 80.degree. C. to about 300.degree.C. and a pressure in the range of from about 100 to about 1000 psig.

49. A process in accordance with claim 45 wherein said zeolite is selected from the group consisting of ZSM-5, ZSM-8, ZSM-11, ZSM-12, ZSM-35, ZSM-38 and combinations thereof.

50. A process in accordance with claim 45 wherein said zeolite is ZSM-5.

51. A process in accordance with claim 45 wherein said zeolite is modified by steam treatment.

52. The process in accordance with claim 45 further comprising a step of modifying a zeolite by acid treatment prior to a step of contacting the hydrogenated product with a catalyst composition comprising said zeolite.

53. A composition produced by the process of claim 45.

54. A process comprising:
contacting a mixture comprising a hydrogenated carbohydrate-containing compound and a hydrocarbon with a catalyst composition comprising a zeolite under a reaction conditions sufficient to form a reaction product containing gasoline boiling range hydrocarbons.

55. The process of claim 54, wherein the hydrogenated carbohydrate-containing compound is sorbitol.

56. The process of claim 54, wherein said hydrogenated carbohydrate-containing compound is lactic acid.

57. The process of claim 54, wherein said hydrocarbon comprises isopentane.

58. The process of claim 54, wherein said hydrogenated carbohydrate-containing compound is selected from the group consisting of ketones, epoxides, diols, glycols, furans, and organic acids.

59. A product produced by the process of claim 54.

60. The process of claim 54, wherein the condition sufficient to form a reaction product containing gasoline boiling range hydrocarbons comprises a temperature in the range of about 200.degree.C. to about 600.degree.C. and a pressure in the range of from about 1 to about 100 psig.

61. The process of claim 54, wherein the reaction conditions comprise a pressure in the range of from about 20 to about 200 psig.

62. A process in accordance with claim 54 wherein said zeolite is selected from the group consisting of ZSM-5, ZSM-8, ZSM-11, ZSM-12, ZSM-35, ZSM-38, and combinations thereof.

63. A process in accordance with claim 54 wherein said zeolite is ZSM-5.

64. A process in accordance with claim 54 wherein said zeolite is modified by steam treatment.

65. The process in accordance with claim 54 further comprising a step of modifying a zeolite by acid treatment prior to a step of contacting a mixture comprising a hydrogenated carbohydrate-containing compound with a catalyst composition comprising said zeolite.

66. The process in accordance with claim 54 further comprising a step of modifying a zeolite by a metal cation prior to a step of contacting a mixture comprising a hydrogenated carbohydrate-containing compound with a catalyst composition comprising said zeolite.

67. The process in accordance with claim 66 wherein said metal cation is selected from the group consisting of zinc, gallium, and nickel.

\* \* \* \* \*